United States Patent
Jin et al.

[11] Patent Number: 6,008,840
[45] Date of Patent: Dec. 28, 1999

[54] APPARATUS FOR INSPECTING ELECTRONIC COMPONENT INSERTION IN A PRINTED CIRCUIT BOARD AND THE METHOD THEREFOR

[75] Inventors: Sang-Hoon Jin, Taegu; Hyeon-Sang Lee, Kyeongsangbuk-do, both of Rep. of Korea

[73] Assignee: Daewoo Electronics Co., Ltd., Seoul, Rep. of Korea

[21] Appl. No.: 08/978,423

[22] Filed: Nov. 25, 1997

[30] Foreign Application Priority Data

Nov. 27, 1996 [KR] Rep. of Korea ............. 96-58057

[51] Int. Cl.⁶ ............................................. H04N 7/18
[52] U.S. Cl. ............................ 348/87; 348/94; 348/95; 348/126; 382/145; 382/147; 382/151
[58] Field of Search ...................... 348/87, 86, 92, 348/94–95, 125, 126, 133, 129–130, 190; 382/141, 145, 144, 147, 149, 151; H04N 7/18

[56] References Cited

U.S. PATENT DOCUMENTS

| | | | |
|---|---|---|---|
| 4,541,011 | 9/1985 | Mayer et al. | 348/133 |
| 4,862,510 | 8/1989 | Duncan et al. | 382/145 |
| 5,214,712 | 5/1993 | Yamamoto et al. | 348/126 |
| 5,398,291 | 3/1995 | Kitakado et al. | 348/126 |
| 5,408,538 | 4/1995 | Kitakado et al. | 348/126 |
| 5,490,084 | 2/1996 | Okubo et al. | 348/87 |
| 5,739,846 | 4/1998 | Gieskes | 348/87 |

Primary Examiner—Vu Le
Attorney, Agent, or Firm—Smith, Gambrell & Russell, LLP

[57] ABSTRACT

The present invention stores digital data of a scanner and includes a component information database for storing information as data of components to be inserted in the printed circuit board and a non-insertion inspection database for storing data of lead wire clinching directions inserted in each hole from predetermined numeric control data. A control section collects hole information as data from the digital data of the scanner, reads the clinching directions of the components inserted in each hole from the non-insertion inspection database, and judges insertion states of the components according to whether or not brightness exists by inspecting a brightness change in the clinching direction around a hole. The present invention inspects brightness while drawing concentric circles from the hole center, inspects whether there is a brightness change around a lead wire direction read from the non-insertion inspection database, and judges a good insertion and a bad insertion according to whether or not the brightness change exists.

1 Claim, 8 Drawing Sheets

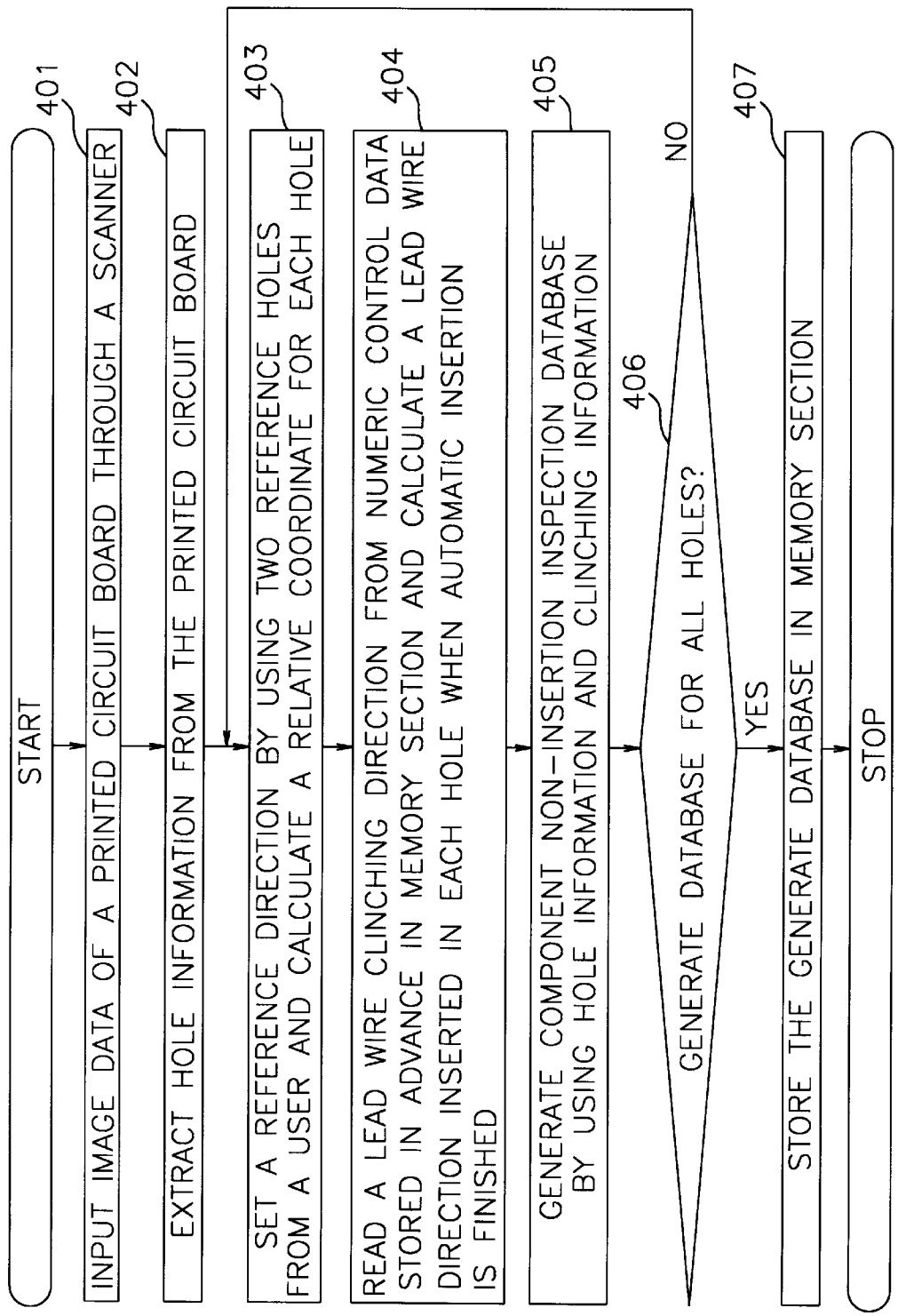

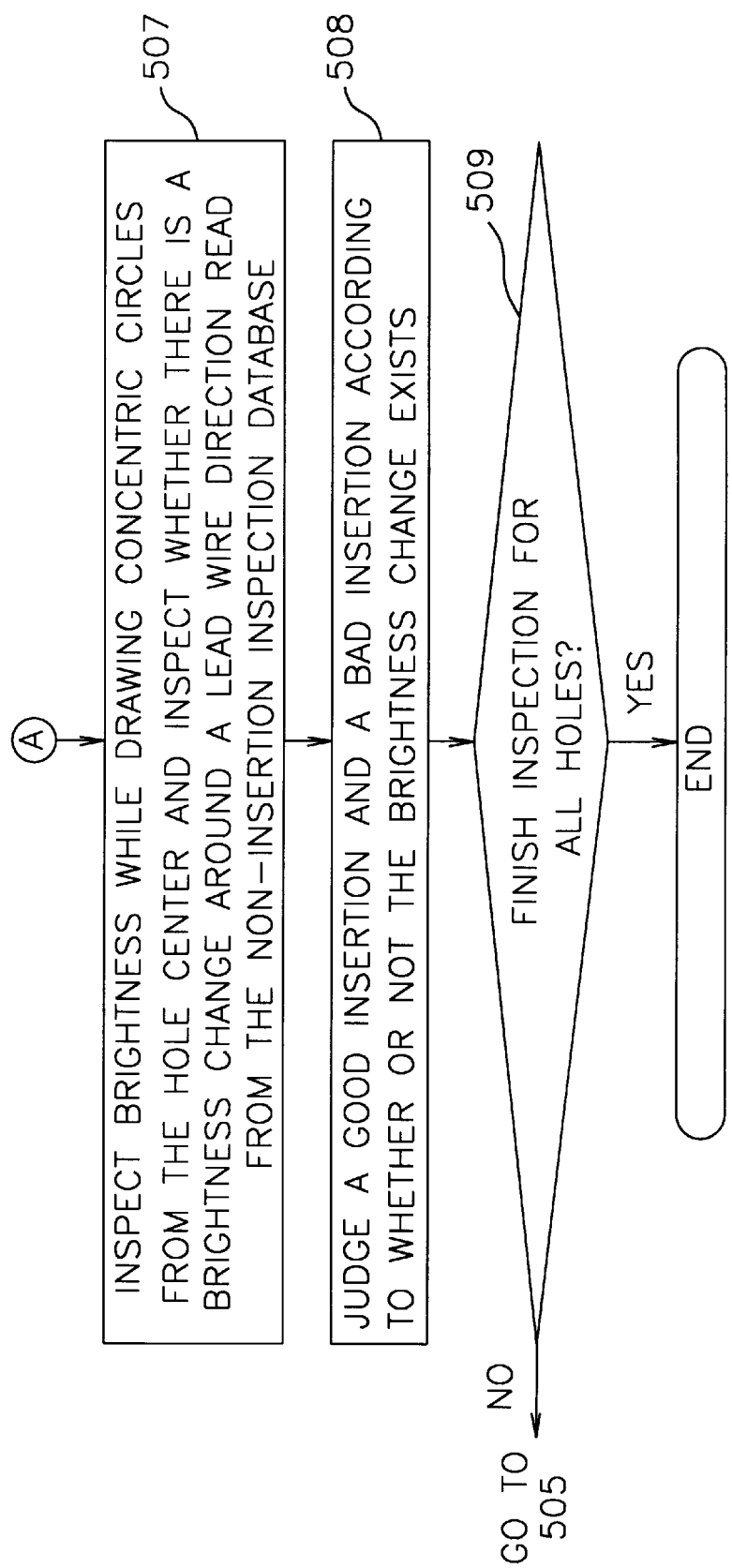

APPARATUS FOR INSPECTING ELECTRONIC COMPONENT INSERTION IN A PRINTED CIRCUIT BOARD AND THE METHOD THEREFOR

BACKGROUND OF THE INVENTION

1. Field of the Invention

The present invention relates to an apparatus for inspecting electronic component insertion in a printed circuit board, and more particularly to an apparatus for inspecting electronic component insertion in a printed circuit board and the method therefor by inspecting a brightness change in clinching directions of component lead wires.

2. Prior Art

Automatic insertion of a component into a printed circuit board for an electronic product production has been attempted from the past, even though the automatic insertion is widely used nowadays. Automatic insertion procedures are performed in the order of (1) making up an electric circuit layout, (2) making up a circuit pattern to be printed on a board based on the electric circuit layout, (3) making up data of components to be inserted into the board according to the printed circuit pattern, (4) collecting information on insertion positions, insertion components, insertion directions, etc., by using the printed circuit pattern and converting the information into numeric control data for each equipment, (5) inputting the numeric control data into an automatic insertion equipment, supplying printed circuit board already made as mentioned above and components required to be automatically inserted for fitting into the printed circuit board, and (6) soldering the component-inserted printed circuit board by using an automatic soldering equipment for completion.

In the procedures as above for a finished printed circuit board, a procedure having a major effect all over the procedures is the one that inspects whether or not the components are inserted. During a series of procedures, unless correction is made to non-inserted or misinserted components before soldering, the uncorrected printed circuit board must be discarded, including the components. Further, the overall procedures for the printed circuit board become wasted.

Accordingly, it is imperative to discover any misinsertion of the components just after making a finished printed circuit board. However, in the past time, there was not a non-insertion inspection method, apart from that using the human eye. An inspection method using the human eye causes the inspection standard to vary depending on a worker's emotional state, work speed and time depend on worker's skill, obtaining a skilled worker is difficult, and a lot of time is required for a worker to become skilled.

In order to solve the problems as mentioned above, holes are detected by taking a picture of printed circuit board before inserting the components by means of a sight inspection equipment, the outer perimeters and the diameters of the holes are calculated to compare them to each other for determining whether the components are inserted into the holes, and maximum and minimum lengths are calculated from the center of each hole to the outer perimeter and determined to be a hole in case that the ratio lies in a criterion range.

In case that the clinched lead wires become adjacent to each other because the holes are made in an adjacent position, a picture of lead wires adjacent to each other is taken to obtain an image. The image is processed by an image processing procedure for an exact insertion inspection. However, a drawback exists in that an exact insertion inspection can not be obtained since adjacent lead wires are determined to be one lead wire.

SUMMARY OF THE INVENTION

In order to overcome the drawback, it is an object of the present invention to provide an apparatus for insertion inspection of electronic component and the method therefor by inspecting an illuminance change in clinching directions of component lead-in wires.

In order to accomplish the above object, the apparatus according to the present invention comprises a scanner, a memory section, a monitor, an input section, a component information database section, a non-insertion inspection database section, and a control section. The scanner converts an image of a printed circuit board to digital data. The memory section stores the digital data from the scanner. The monitor displays the digital data on the screen. The input section inputs data and commands from a user. The component information database section stores component information to be inserted in the printed circuit board. The non-insertion inspection database section stores a non-insertion inspection database including a clinching direction data for the components inserted in respective holes from numeric control data which is predetermined. The control section collects hole information from the digital data of the scanner, reads the clinching directions of the components inserted in each hole from the non-insertion inspection database section, and judges the insertion state of the components according to whether or not brightness exists by inspecting a brightness change in the clinching direction around a hole perimeter.

Further, the method for insertion inspection of electronic component according to the present invention comprises a step for collecting hole information by processing an image of a printed circuit board scanned by a scanner, a step for reading a non-insertion inspection database in a memory section, searching for two reference holes from the printed circuit board, and readjusting the non-insertion inspection database of each hole to meet the printed circuit board, a step for calculating a hole perimeter of the printed circuit board, inspecting whether a ratio of the hole perimeter versus a hole length lies in a range wherein the ratio is read from the non-insertion inspection database, calculating a minimum value $D_{min}$ and a maximum value $D_{max}$ of a length from the hole center to the hole perimeter, and checking whether the ratio lies in the following range:

$$0.75 \leq D_{min}/D_{max} \leq 1.5;$$

and a step for inspecting brightness while drawing concentric circles from the hole center, inspecting whether there is a brightness change around a lead wire direction read from the non-insertion inspection database, and judging a good insertion and a bad insertion according to whether or not the brightness change exists.

BRIEF DESCRIPTION OF THE DRAWINGS

The above objects and other advantages of the present invention will become more apparent by describing in detail a preferred embodiment thereof with reference to the attached drawings in which:

FIG. 8 is a flow chart for showing component non-insertion inspection database generation procedures according to an embodiment of the present invention;

DETAILED DESCRIPTION OF THE PREFERRED EMBODIMENT

Description will be made in detail below with reference to the accompanying drawings.

Figure 1:
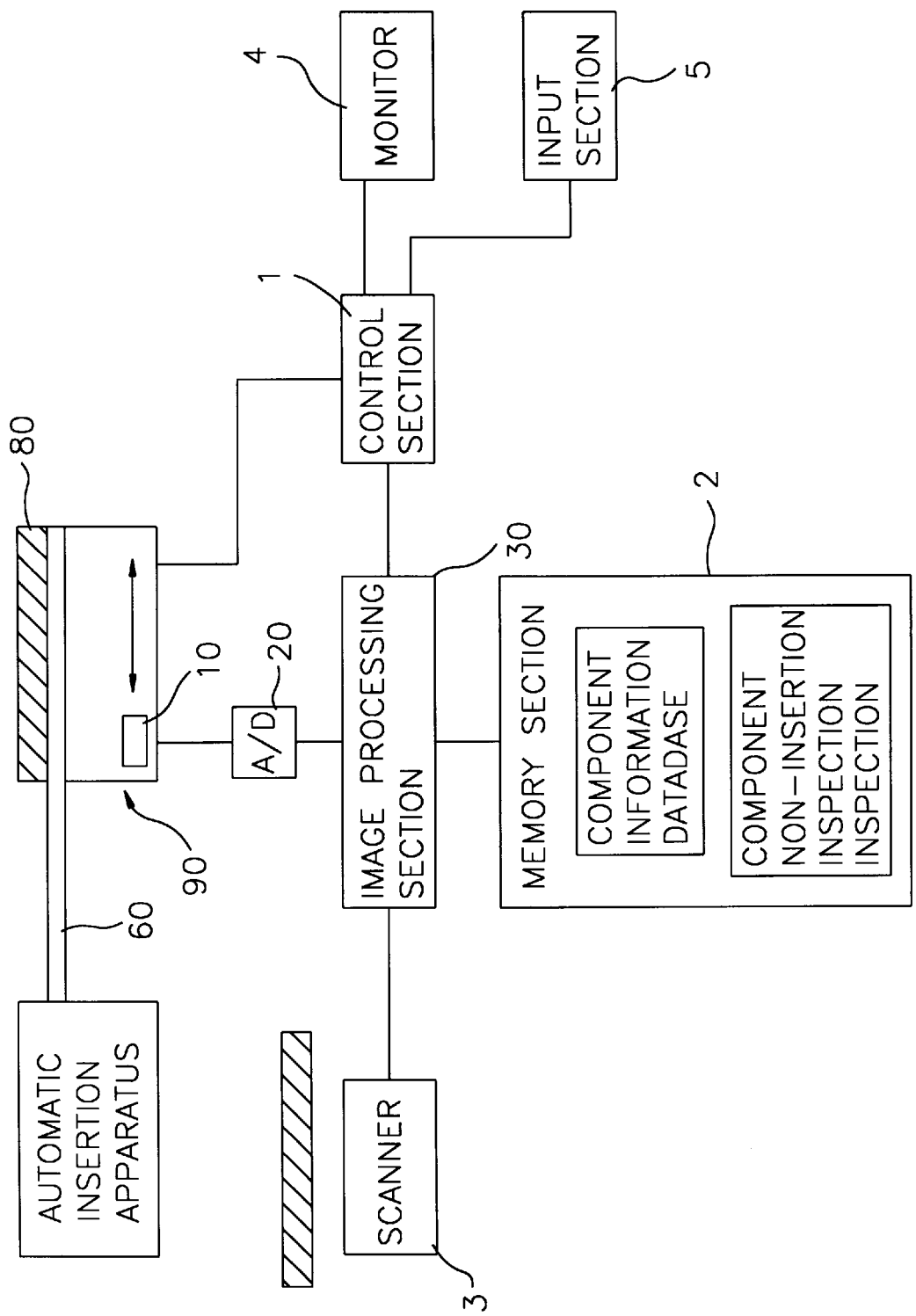
FIG. 1 is a block diagram for showing an apparatus for inspecting electronic component insertion in a printed circuit board according to an embodiment of the present invention.

FIG. 1 is a block diagram for showing an apparatus for inspecting electronic component insertion in a printed circuit board according to an embodiment of the present invention. As shown in FIG. 1, the apparatus according to the embodiment of the present invention comprises a control section 1, a memory section 2, a scanner 3, a monitor 4, an input section 5, a non-insertion inspection database section 6, and a component information database section 7. The scanner 3 converts an image of a printed circuit board to digital data. The memory section 2 stores the digital data from the scanner 3. The monitor 4 displays the digital data on the screen. The input section 5 inputs data and commands from a user. The component information database section 7 stores component information to be inserted in the printed circuit board. The non-insertion inspection database section 6 stores a non-insertion inspection database including a clinching direction data for the components inserted in respective holes from numeric control data which is already made.

When automatic insertion equipment inserts components, each equipment inserts a component after rotating a printed circuit board (PCB) at a certain angle, in general. Therefore, lead wires of components are clinched in different clinching directions. Further, each equipment for automatic insertion has its own clinching direction.

Figure 2:
FIG. 2 to FIG. 6 are lead wire clinching directions for each component and for each equipment.
Figure 3:
Figure 4:
Figure 5:
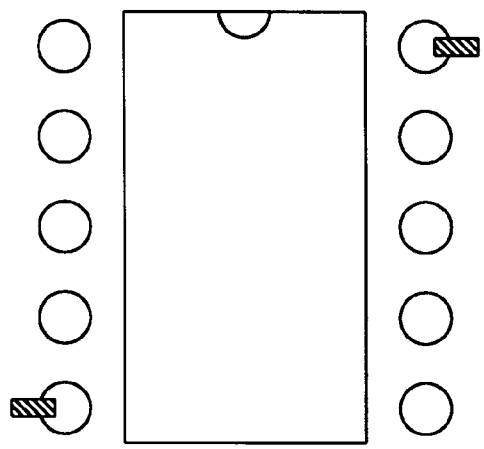
Figure 6:
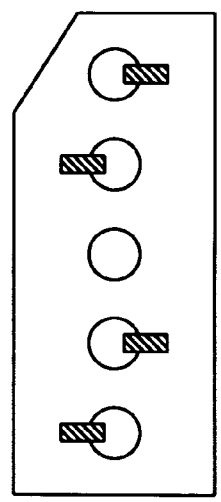
Figure 7:
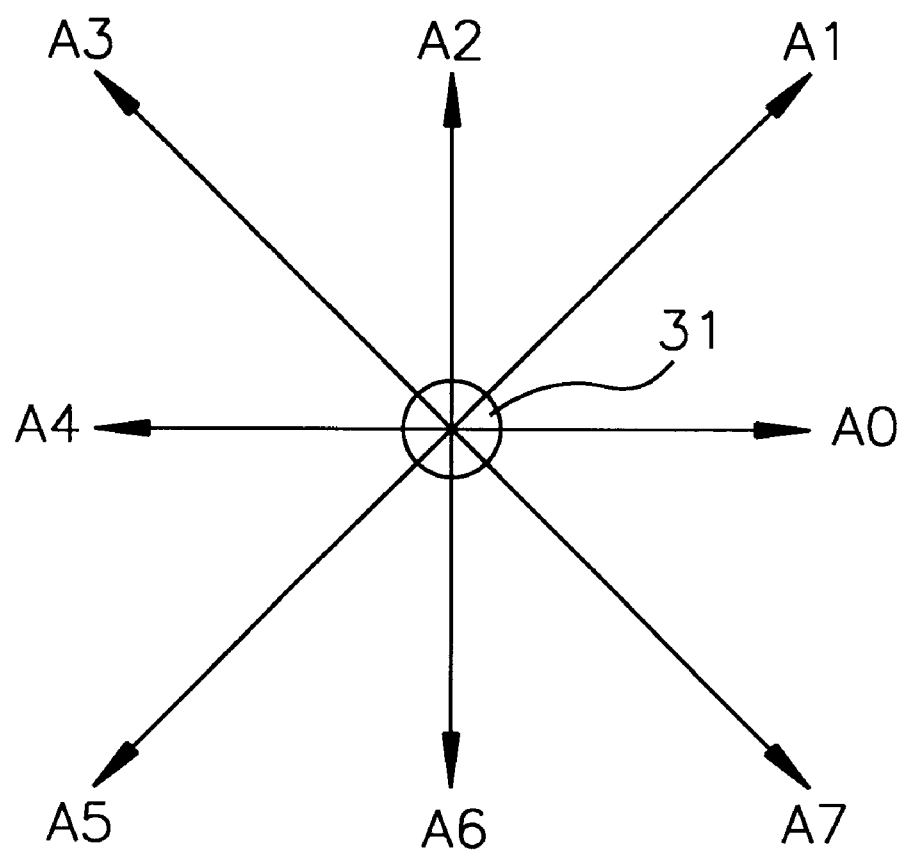
FIG. 7 shows lead wire clinching directions after an automatic insertion equipment has inserted a component into a printed circuit board.

FIG. 2 to FIG. 6 are lead wire clinching directions for each component and for each equipment. FIG. 2 shows clinching directions of lead wires of a radial component, FIG. 3 shows clinching directions of the radial component when an equipment different from that used in FIG. 2 is used for automatic insertion. FIG. 3 shows clinching directions of the radial component when an equipment different from those used in FIGS. 2 and 3 is used for automatic insertion. FIG. 5 shows clinching directions of lead wires of an integrated circuit (IC) chip. FIG. 6 shows clinching directions of lead wires of a connector. FIG. 7 shows lead wire clinching directions after an automatic insertion equipment has inserted a component.

Lead wires of a component after an automatic insertion equipment has inserted the component can be clinched in 8 directions A0, A1, A2, A3, A4, A5, A6, and A7 spaced by 45° among them. Reference numeral 31 denotes a hole formed in a printed circuit board.

Operations of the apparatus as above will be described in detail below.

A non-insertion inspection method according to the embodiment of the present invention comprises procedures for an inspection database generation and for a component inspection. The procedure for an inspection database generation is accomplished on an off-line basis before executing automatic insertion, and inspection for the automatic insertion is executed for all printed circuit boards every time the automatic insertion is finished. At this time, the printed circuit board having non-inserted components is transferred to a separate position by a main processor, and correction job is performed by using position information about non-insertion holes found by a non-insertion equipment.

The procedure for an inspection database generation is performed as follows. That is, a printed circuit board 80, which is a subject, arrives on an optical section 90 by a conveyer 60. A cover of the optical section 60 is made of glass, and a lighting section provides light and a transfer section transfers the camera section 10 for scanning the printed circuit board 80, so that a camera of the camera section 10 takes a picture of an image of the printed circuit board 80. The image of the printed circuit board 80 placed on the optical section 90 is taken by the camera section 10 and the image is outputted to an analog/digital converter 20. The analog/digital converter 20 inputs an image signal of the printed circuit board 80 and converts the image signal to digital data. The digital data is outputted to an image processing section 30. The image processing section 30 executes image processing procedures for binary coding and hole perimeter detection. The result of the image processing procedures of the image processing section 30 is outputted to the controller 1. The controller 1 inputs image processing data from the image processing section 30, collects data necessary for recognition from a printed circuit board which has missing components, and stores the collected data in a memory section 2.

Figure 10:
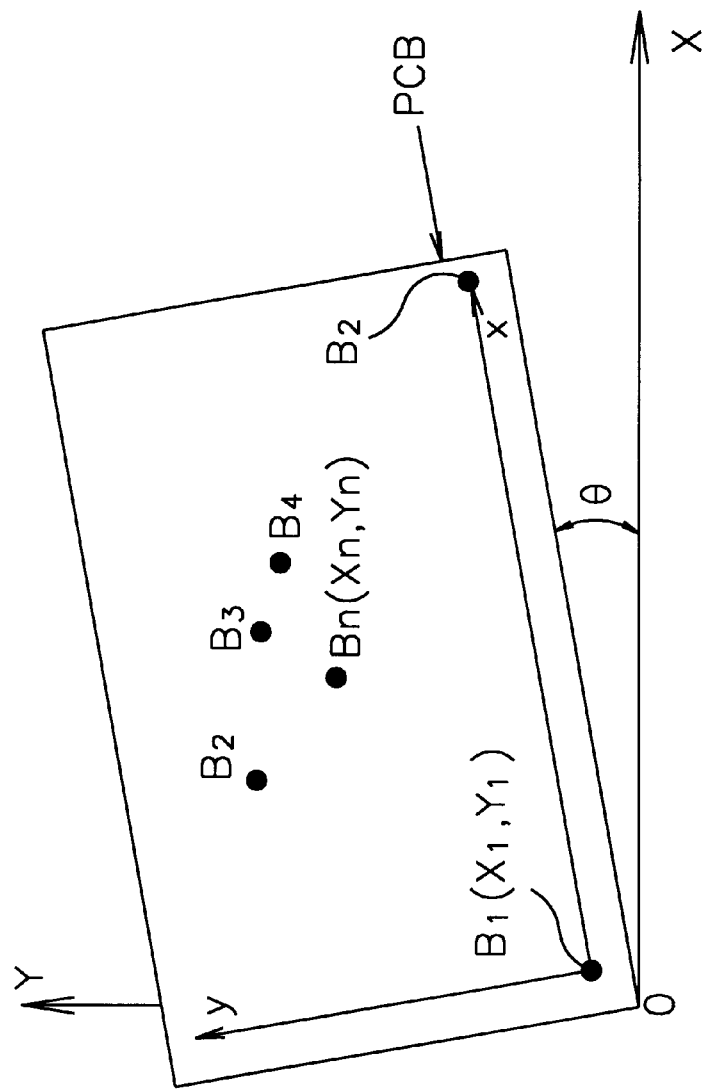
FIG. 10 is a view for explaining generation of hole information database.

FIG. 10 is a view for explaining generation of hole information database.

The relative coordinate calculated as above is converted to a relative coordinate THn(TXn, TYn) with respect to a reference vector B. When converted, the reference vector B is set up with respect to a reference of two hole centers [B1(X1, Y1), B2(X2, Y2)] which a user freely chooses. Another arbitrary hole center Bn(Xn, Yn) except for the reference holes is displaced by (−X1, −Y1) and rotated in a clockwise direction by an angle θ with respect to the X axis. The relative coordinate THn(TXn, TYn) is stored as data in a database in the memory section 2. A database format is constructed as follows:

| serial no. | degree of hole | center point TH (pixel number, pixel number) | length (pixel number) | diameter (pixel number) |
|---|---|---|---|---|
| 1 | 1 | 100, 100 | 15 | 5 |
| . | . | . | . | . |
| . | . | . | . | . |
| data of B1 | degree of B1 | absolute coordinate (X1,Y1) | length of B1 | diameter of B1 |
| data of B2 | degree of B2 | absolute coordinate (X2,Y2) | length of B2 | diameter of B2 |

After generating a database by extracting hole information as above, a clinching direction of a lead wire inserted in each hole is read from the numeric control data stored in the memory section 2. Further, a lead wire direction for each hole is read when automatic insertion is completed. Accordingly, a database for inspecting non-insertion of a component is generated by using the hole information and clinching direction information.

FIG. 8 is a flow chart for showing component non-insertion inspection database generation procedures according to an embodiment of the present invention.

As shown in FIG. 8, at step 401, image data for a printed circuit board is inputted through the scanner 3, so that the image is displayed on the monitor 4. At step 402, hole information is extracted by using an image recognition algorithm. At step 403, relative coordinates for each hole are calculated with a reference direction set up by using reference holes. At step 404, a direction of a lead wire inserted in each hole is calculated, as automatic insertion is finished, by reading lead wire clinching directions from the numeric control data which is stored in advance in the memory section 2. At step 405, the component non-insertion database is generated by using hole information and lead wire clinching information. At step 406, it is judged that a database for all holes is generated. In case that the database is not generated for every hole, the step 403 is repeated. In case that the database for all holes is generated, the generated database is stored in the memory section 2 at step 407, and the database generation program is ended.

Component non-insertion inspection is performed by inspecting whether there is a hole indicated as data of the database which are obtained in advance by inputting an image of a printed circuit board of a subject.

At first, a length from the hole center to the outer perimeter is inspected and a ratio of the length with respect to a length calculated in the database is inspected within a predetermined range. In case of an ideal hole, both the means and deviation of length values from the center hole to the outer perimeter become zero. The means and deviation increases as a hole goes away from a circle. The deviation for length values from the hole center to the outer perimeter is calculated and a value $D_{err}$ regulated with respect to a mean length is calculated. When the value $D_{err}$ is larger than a predetermined value, a determination is made for a lead wire to be inserted since it is not considered as a hole.

$$Davrg = \frac{1}{N}\sum_{n=1}^{N} D(n)$$

$$Ddist = \frac{1}{N}\sum_{n=1}^{N} [D(n) - Davrg]^2$$

$$Derr = \frac{Ddist}{Davrg^2} > TH$$

here, n≠1, 2

D(n): Distance from a hole center to a $n^{th}$ pixel on the outer periphery,

N: The number of total pixels, $D_{avrg}$: mean length value, $D_{dist}$: distribution value, $D_{err}$: a regulated value with respect to a mean length Here, the distribution value can be an indicator which shows an order of distortion with respect to an ideal circle. If a hole has a shape of an ideal circle, the distance information D(n) is concentrated around the mean length value $D_{avrg}$. As the distortion of a hole circle becomes larger, the distance information D(n) is distributed over a wide range. Accordingly, the distribution can be an efficient indicator which shows a degree of distortion of a circle. Further, a ratio of a distribution with respect to the mean length value powered by 2 becomes a regulated value with respect to a circle size.

Figure 9A:
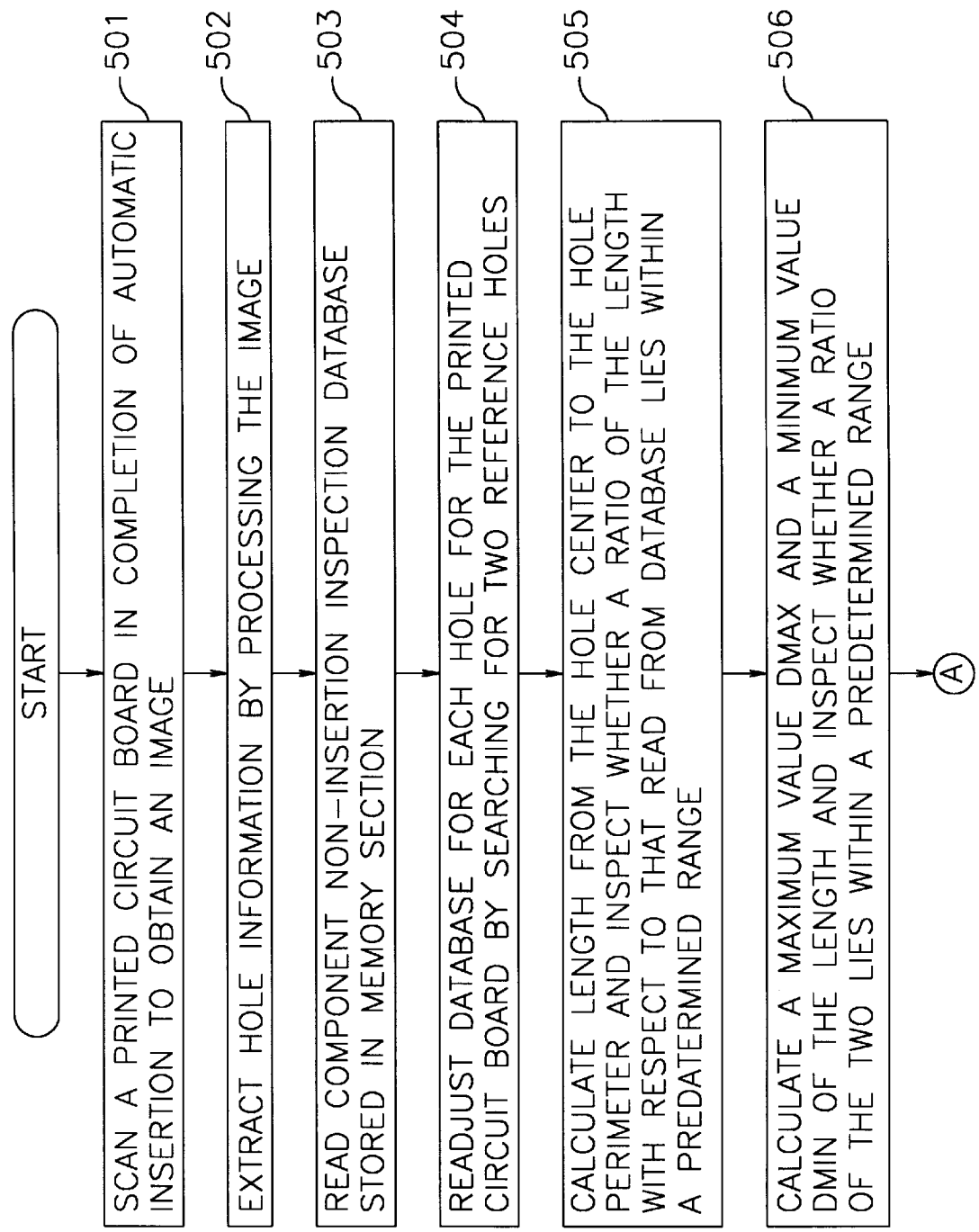
FIG. 9 is a flow chart for controlling an apparatus for inspecting electronic component insertion in a printed circuit board according to an embodiment of the present invention.

FIG. 9 is a flow chart for controlling an apparatus for inspecting electronic component insertion in a printed circuit board according to an embodiment of the present invention. As shown in FIG. 9, at step 501, a printed circuit board to be inspected is conveyed onto a scanner 3 for obtaining an image of the printed circuit board. At step 502, hole information is extracted by processing the image obtained at step 501. At step 503, the non-insertion inspection database stored in the memory section 2 is read. At step 504, two reference holes are selected from the printed circuit board, and database for each hole are readjusted for the printed circuit board. At step 505, a length from a hole center to a hole perimeter is calculated, and a ratio of the length with respect to that read from the database is inspected to lie within a predetermined range. At step 506, a maximum length $D_{max}$ and a minimum length $D_{min}$ from the hole center and the hole perimeter are calculated, and a ratio of the two lengths are inspected to lie with the predetermined range as follows:

$$0.75 \leq D_{min}/D_{max} \leq 1.5$$

At step 507, brightness is inspected while drawing concentric circles from the hole center to judge whether a brightness change exists around a lead wire direction read from the non-insertion inspection database. At step 508, a good insertion and a bad insertion are judged according to whether or not the brightness change exists, and the result is stored. At step 509, a determination is made whether the inspection is finished for all holes, and the step 505 is repeated in case that the inspection is not finished for all holes and the inspection is completed in case that the inspection is finished for all holes.

As described above, with the present invention which inspects insertion states according to whether or not the brightness change exists, misjudging the insertion by adjacent lead wires can be prevented. Productivity can be improved by performing the inspection automatically rather than manually, keeping and transporting of data can be easily achieved by managing the data with a computer, and efficient correction work and productivity management are obtained for the future use by computerization.

What is claimed is:

1. A method for inspecting electronic component insertion in a printed circuit board, comprising the steps of:

collecting hole information as hole data by processing an image of the printed circuit board scanned by a scanner, reading a non-insertion inspection database in a memory section, searching for two reference holes from the printed circuit board, and readjusting the non-insertion inspection database of each hole for the printed circuit board, calculating a length from a hole center to a hole perimeter, inspecting whether a ratio of the length with respect to that read from the non-insertion inspection database lies in a predetermined range, calculating a minimum length value $D_{min}$ and a maximum length value $D_{max}$ from the hole center to the hole perimeter, and checking whether the ratio lies in the following range:

$$0.75 \leq D_{min}/D_{max} \leq 1.5;$$

and inspecting brightness while drawing concentric circles from the hole center, inspecting whether there is a brightness change around a lead wire direction read from the non-insertion inspection database, and judging a good insertion and a bad insertion according to whether or not the brightness change exists.

* * * * *